United States Patent [19]

Tomei

[11] 4,049,494
[45] Sept. 20, 1977

[54] VACCINE PRODUCTION PROCESS

[75] Inventor: L. David Tomei, Buffalo, N.Y.

[73] Assignee: The United States of America as represented by the Secretary of Agriculture, Washington, D.C.

[21] Appl. No.: 610,472

[22] Filed: Sept. 4, 1975

[51] Int. Cl.$^2$ .......................... C12K 7/00; C12B 3/00; A61K 39/26
[52] U.S. Cl. ..................... 195/1.1; 195/1.4; 195/1.8; 424/89
[58] Field of Search .................. 195/1.1, 1.4, 1.8; 424/89

[56] References Cited

U.S. PATENT DOCUMENTS

| 3,196,077 | 7/1965 | Pilz et al. | 195/1.1 |
|---|---|---|---|
| 3,836,626 | 9/1974 | Lavender | 195/1.8 |

OTHER PUBLICATIONS

Willmer–Cells and Tissues in Culture, vol. 1 (1965) pp. 299–301.

Primary Examiner—Sam Rosen
Attorney, Agent, or Firm—M. Howard Silverstein; William E. Scott; David G. McConnell

[57] ABSTRACT

A viral vaccine effective against foot-and-mouth disease is produced without the use of serum or non-chemically defined serum substitutes. A viable culture of baby hamster kidney cells in a heat-stable, glutamine-free, serum-free, chemically defined medium is inoculated with one of the seven major immunological types of foot-and-mouth disease viruses to which the cells are susceptible, the virus is propagated in the culture and the virus harvest is recovered therefrom.

4 Claims, No Drawings

VACCINE PRODUCTION PROCESS

This invention relates to the production of vaccines from viruses propagated in mammolian cells adapted to and continuously grown in a serum-free, chemically defined medium. More particularly, it relates to the propagation of all seven major immunological types of foot-and-mouth disease virus in baby hamster kidney cells adapted to and continuously grown in a heat-stable, glutamine-free, serum-free chemically defined medium and to the production of vaccines useful in the prevention of foot-and-mouth disease.

Viral vaccines for veterinary use are produced from cultures of animal cells that are used as hosts for the proliferation of virus. Established cell lines such as baby hamster kidney (BHK-21) are commonly used for the large-scale production of vaccines in many countries. In all instances, cells must be grown in nutrient media supplemented with either animal serum or chemically undefinable nutrients such as lactalbumin hydrolysate and tryptose phosphate broth to stimulate cell growth and maintain continuous cultures.

The current state of the art of vaccine production is such that virus propogation in these processes requires host cells grown in serum-supplemented media. The use of serum in cell culture growth media has presented may problems with regard to vaccine production. Serum is a source of bacterial, viral and fungal contaminants in cell cultures. Low temperature storage is required. Specific steps which are time consuming and costly are required in the preparation and sterilization of media. Special vessels to mix the serum with the synthetic components and sterilization by membrane filtration instead of autoclaving because of heat labile components are also required.

The availability and cost of serum are serious obstacles in vaccine production. The quality of serum varies considerably in all areas of the world and is often not easily obtainable in the quantities necessary for large-scale vaccine production. In addition, serum can account for 80% of the total cost of nutrient media.

Postvaccinal allergic responses caused by the presence of residual antigenic serum proteins can be a significant problem in the use of vaccines produced using serum-supplemented cell culture media. Elution of serum proteins from cultured cells is difficult and often ineffective and, therefore, they are carried over into the final virus harvest. Immediate allergic responses and hypersensitization caused by the presence of residual serum proteins in vaccine have been reported in animals receiving BHK vaccines against foot-and-mouth diseases. Elimination of these unwanted antigens requires additional purification steps in the production process that substantially increase production costs. Consequently, the development of a strain of cells that is not serum dependent and that remains susceptible to foot-and-mouth disease virus infection represents the ideal solution to the above noted problems associated with the use of serum in vaccine production processes.

Therefore, it is an object of this invention to provide a new and improved method of producing vaccines effective against foot-and-mouth disease.

Another object is to produce foot-and-mouth disease virus in a cell culture that is completely free of serum and serum substitutes of a chemically undefinable nature.

A further object is to produce foot-and-mouth disease virus in a heat stable, glutamine-free, serum-free, chemically defined media.

A still further object is the development of a vaccine production process using cells adapted to a chemically defined media.

In general, according to this invention, the above objects are accomplished by a process in which mammalian cells such as baby hamster kidney cells grown on and adapted to a heat-stable, glutamine-free, serum-free, chemically defined medium are inoculated with one of the seven immunological types, A, O, C, SAT-1, SAT-2, SAT-3, or Asia, of foot-and-mouth disease virus. The viruses are allowed to propogate within the BHK cells on the chemically defined medium until a peak yield is reached after which the virus is harvested and processed into a vaccine.

As described in Biotechnology and Bioengineering, 17, 765–778, 1975, the cells used in this invention originated from cells identified as clone 13 of BHK-21 which had been adapted to chemically defined medium. These cells were designated BHK-S. Details of the origin of the BHK cells and other information regarding the production process is adequately described in the above reference which will hereafter be considered incorporated as part of this invention into this specification.

Producing vaccines by the process of this invention has many advantages over presently available methods. In the process of this invention, the growth of mammalian cells, the infection or inoculation of these cells and the proliferation of viruses for the production of live, modified, attenuated, or dead virus vaccines occurs in a nutrient medium completely free of serum and non-chemically definable serum substitutes. The medium can be sterilized by autoclaving and it can be stored as a liquid or as a dry powder. The cost of chemically defined media is less than that of serum supplemented media and quality control is not as troublesome. In addition, vaccine made by the process of this invention is free of serum associated antigens and bacterial, viral and fungal contaminants.

Although this invention is exemplified with foot-and-mouth disease viruses, the process is applicable to other viruses. Any virus to which the cell culture is susceptible can be grown in the same manner and vaccine produced.

For the purposes of this invention, foot-and-mouth disease viruses of all seven immunological types obtained from three different sources, cell lines, primary cultures, and animal lesions, were used to inoculate the cells on the chemically defined medium.

BHK-S cells were grown in a heat-stable, glutamine-free, serum-free, chemically defined medium. The composition of the particular medium used for this invention is shown in Table 1. The composition of this particular medium does not necessarily represent a critical formulation because other formulations may also be used. The formulation is determined by the nutritional requirements of the particular cell line. The medium was sterilized by autoclaving for 30 minutes (120°C, 15 psi) at pH 4.3 and stored at 4°C until used. Cell enumeration and viability were determined by phase microscopy and counting chambers designed for use with phase microscopes. Stock cultures of 600 to 1000 ml. were maintained in 1000 ml. spinner flasks at 35°C with an agitation rate of 104 r.p.m.

Foot-and-mouth disease virus types $A_{24}$, $O_1$, and $C_3$, originally isolated from bovine tongue were propagated in cultures of primary bovine kidney (BK) cells for seven passages; and in roller bottle monolayer cultures of BHK-21, obtained from the American Type Culture Collection, Rockville, Md., for two passages. Strains of foot-and-mouth disease virus, types Aisa, SAT-1, and SAT-2 received five passages in BK cells; SAT-3 received one passage in lamb testes cells and two passages in BK cells. All virus preparations were stored at −70°C until used. Foot and Mouth disease virus $A_{24}$, $O_1$ and $C_3$, which had been passaged only in cattle by intradermal-lingual inoculation, were also used to infect BHK cells. Bovine tongue epithelium was ground with sterile alundum in Hanks' lactalbumin hydrolysate medium with 1000 units/ml. of penicillin and 1000 micrograms/ml. of streptomycin and centrifuged at 200 × g (gravity) for 10 minutes to remove tissue debris and alundum. The supernatent was then used to inoculate the cell cultures.

Cells used for virus experiments were centrifuged at 180 × g for 5 minutes and resuspended in fresh media (pH 7.3 to pH 7.5). Cultures were dispensed in 100 ml. volumes, inoculated, and incubated at 37°C on an orbital shaker operated at 140 r.p.m. Samples for virus assay were taken at specific time intervals and centrifuged at 250 × g for 10 minutes at 4°C. The supernatant was decanted and stored at 4°C until assayed. Infectivity titers were determined within 12 hours and complement fixing titers within 14 days. The pH of each culture was maintained at 7.3 to 7.8 by dropwise addition of 1 N NaOH.

Vaccines were made by resuspending BHK cells in 100 ml. volumes of fresh media at a concentration of 4.0 × $10^6$ cells/ml and inoculating with 0.1 plaque forming units per cell of the foot-and-mouth disease virus, types $A_{24}$, $O_1$ and $C_3$, passaged seven times in BK cells and twice in BHK cells as previously described. The cultures were treated as described above, and the viruses were harvested 12 hours after inoculation, assayed, and stored at 4°C for 30 hours before they were inactivated. Acetylethyleneimine was added to each harvest (0.05% v/v), and the virus inactivated for 72 hours at 25°C with constant mixing. Samples were taken for infectivity assay at the start of the inactivation and at 30, 60, and 90 minutes and 24 hours after acetylethyleneimine was neutralized in the samples by adding sodium thiosulfate to a final concentration of 2%w/v.

Equal volumes of aqueous material were mixed with incomplete Freund's adjuvant, prepared by mixing 9 parts of Marcol 52 (a white mineral oil of national formulary grade with a viscosity of not more than 37 centistokes at 100°F and a specific gravity range of 0.818 to 0.880 at 77°F.) and 1 part Arlacel A (mannide monooleate, purest grade for use in human and veterinary adjuvant formulations) and filtering through a 0.45μ filter. The water-in-oil emulsions were prepared in a blendor, and 0.5% (v/v) chloroform was added to each batch as a bacteriocide.

Vaccines were administered subcutaneously in the nape of the neck in 1-ml doses to 400- to 500-gram Hartley strain guinea pigs and injected into the dorsal region of the neck in 5-ml doses to approximately 400-kg grade Hereford steers.

At 30 days postvaccination, the guinea pigs were bled by cardiac puncture; steers were bled at 55 days postvaccination by jugular venipuncture. Blood samples were allowed to clot at 25°C and then centrifuged at 250 × g at 4°C, and serum was harvested and stored at −20°C. Sera were heat inactivated at 56°C for 30 minutes before they were assayed in a neutralization test with suckling white mice (for details see Can. J. Comp. Med., 27, 193, 1963) or a plaque-reduction neutralization test. Titers were calculated as the reciprocal of the $log_{10}$ 50% protective dilution ($PD_{50}$) or as the reciprocal of the log of the serum dilution producing 70% reduction of the number of plaques.

At 56 days postvaccination, the steers were separated into two groups of three in two isolation rooms, and two control steers were added to each group. The three vaccinated steers and one control steer in each group were inoculated intradermal-lingual with 1 ml of a dilution of foot-and-mouth disease virus $O_1$ Caseros (of bovine origin, without cell culture passage) calculated to contain $10^{4.0}$ bovine 50% infective doses. The inoculum was administered in four sites intradermal-lingual. The other control animal in each group acted as a contact control. The rectal temperature of the steers was taken daily, and the steers were checked for visible clinical lesions at 3, 6, 9 and 13 days after challenge.

Growth curve experiments using foot-and-mouth disease virus types $A_{24}$, $O_1$ and $C_3$ in BHK-S cells at two multiplicities of infection, $10^{-2}$ and $10^{-7}$ plaque forming units per cell with a cell concentration of 1.7 × $10^6$ cells/ml in glutamine-free, serum-free, chemically defined medium. Peak infectivity titers of 8.10 ($log_{10}$ plaque forming units per cell/ml) were observed at 12 to 16 hours after infection with each of the three virus types at a multiplicity of $10^{-2}$ plaque forming units per cell. As the multiplicity of infection was decreased to $10^{-7}$ plaque forming units per cell, the time of peak infectivity was correspondingly increased to between 20 and 24 hours. However, neither the peak infectivity nor the rate of virus production was substantially changed.

BHK-S cultures were inoculated with type $C_3$ Resende at multiplicities of infection ranging from 0.003 to 3.3 plaque forming units per cell and there was no substantial difference in peak infectivity titers. Maxima were reached at 10 hours for 3.3 and 0.33 plaque forming units per cell. The rate of virus production was comparable at all multiplicities of infection.

The results show that even when only very low levels of virus are available, it is possible to use the process of this invention to infect the cell culture and obtain good virus propagation and a good harvest with which to make a vaccine.

As shown in Table 2, the cell concentration in the process of this invention is not critical and it is not necessary to concentrate cells or collect them on a surface as is done in other processes. This simplifies the process greatly by allowing the direct inoculation of cells with the virus. Foot-and-mouth disease virus (FMDV) type $C_3$ Resende was used at a multiplicity of infection of approximately $10^{-1}$ plaque forming units/cell. A fivefold increase in the cell concentration produced a tenfold increase in peak infectivity and a fourfold increase in complement-fixing (CF) titer. Peak CF titers were observed 4 to 9 hours after peak infectivity at the lowest and intermediate cell concentration.

A comparison of the rates of virus production and peak infectivity titers on BHK-S cells grown in chemically defined media and cells designated BHK-R grown in serum-supplemented media (BHK-R cells originated from cells identified as clone 13 of BHK-21 which were received at the 124th passage and were grown in Joklik-modified MEM medium supplemented with 10% heat-inactivated fetal bovine serum) showed no substantial differences.

Cytopathogenic effect as estimated by loss in cell viability in cultures infected at multiplicities of infection of 3.3 and 0.033 plaque forming units/cell and caused by foot-and-mouth disease virus $C_3$ Resende was greater in BHK-S cells than in BHK-R cells. At multiplicities of infection of 3.0 to 3.3 plaque forming units/cell, a 50% cytopathogenic effect was noted in BHK-R cells at 20 hours after inoculation and a 95 to 100 % cytopathogenic effect in BHK-S cells at 12 hours indicating that it is easier to infect the BHK-S cells.

The susceptibility of BHK-S cells to Asis-1 and SAT-type viruses was determined by inoculating cultures of $1.8 \times 10^6$ cells/ml at multiplicities of infection of approximately $10^{-2}$ plaque forming units/cell.

Virus was harvested when cell viability declined to $\leq 30\%$, 20 to 23 hours after inoculation. As seen in Table 3, the BHK-S cell is suceptible to infection with Asia-1 and SAT-type viruses. Prior passage in BHK-21 cells or primary BK cells is not necessary for the production of high titers in the BHK-S cultures as shown by the results in Table 3 of inoculating with bovine tongue epithelium preparations of $A_{24}$, $O_1$ and $C_3$ foot-and-mouth disease virus types.

Viruses for use in experimental vaccines were harvested when loss in cell viability was $\geq 95\%$. As shown in Table 4, all viruses had infectivity titers $\geq 8.5$ $\log_{10}$ plaque forming units/ml and CF titers $\geq 1:24$. The viruses were then inactivated with acetylethyleneimine and first-order inactivation kenetics were observed with calculated titers of about $10^8$ plaque forming units/ml at 24 hours for all three viruses. All inactivated viruses retained their original CF titers, and no infectious virus was observed through three blind passages in primary BK cell cultures. After being held for 21 days at 4°C the inactivated viruses retained their original CF titers. They were then incorporated into monovalent and trivalent vaccines.

All animals receiving the vaccines developed neutralizing antibodies as shown in Tables 5 and 6. Titers ($\log_{10}$ 50% Protective Dilution) in steers, as assayed in suckling mice, ranged from 1.45 to 2.65 for all three viruses, with mean titers of 2.01 against $A_{24}$, 2.28 against $O_1$, and 1.91 against $C_3$. Mean plaque-reduction neutralization test titers were 0.67, 0.31 and 0.45 $\log_{10}$ higher than those previously reported in suckling mice for $A_{24}$, $O_1$, and $C_3$, respectively.

Generalized foot-and-mouth disease was noted in all control animals and in none of the vaccinated steers after intradermal-lingual challenge. None of the vaccinates had a febrile response during a 13 day observation period. Only two lesions were observed in the vaccinated steers. One was a local lesion at the site of inoculation in steer number 5, and the other was a vesicular lesion on the coronary band on the heel of the right rear foot of steer number 1. The steers were sacrificed at 13 days postvaccination and the vaccination sites examined. All the steers had minimal local reactions. Four animals had evidence of subcutaneous vaccination and two had both subcutaneous and intramuscular depots of vaccine. The maximal reaction measured approximately $2 \times 4 \times 1$ cm, but the others consisted of a diffuse area approximately $1 \times 2$ cm $\times 3$ mm, each with a series of minute ($\sim 2$ mm) granulomatous areas.

Tests to determine the stability of the foot-and-mouth disease antigens in the glutamine-free, serum-free, chemically defined medium were conducted. The results showed that the virus in the chemically defined medium was as stable as virus in a medium supplemented with serum at 4°C for a 70-day observation period and at 37°C for a 30 hour observation period.

TABLE 1

| Component | Conc. mb/L | Component | Conc. mg/L |
|---|---|---|---|
| Amino acids | | Salts, etc. | |
| L-Alanine | 400 | NaCl | 7400 |
| L-Arginine . HCl | 100 | KCl | 400 |
| L-Asparagine | 300 | $CaCl_2$. $2H_2O$ | 265 |
| L-Cysteine . HCl | 75 | Ferric ammonium citrate | 3 |
| L-Glutamic Acid | 150 | $MgCl_2$. $6H_2O$ | 275 |
| L-Histidine . HCl | 60 | $NaH_2PO_4$. $H_2O$ | 300 |
| L-Isoleucine | 150 | $ZnSO_4$. $7H_2O$ | 0.3 |
| L-Leucine | 300 | Phenol red | 10 |
| L-Lysine | 300 | Methylcellulose, 15 cps | 500 |
| L-Methionine | 60 | $NaHCO_3$ | 1000[1] |
| L-Phenylalanine | 120 | Vitamins[2] | |
| L-Proline | 300 | D-Biotin | 1 |
| L-Serine | 300 | Choline . Cl | 50 |
| L-Threonine | 135 | Folic acid | 1 |
| L-Tryptophan | 60 | Niacinamide | 1 |
| L-Tyrosine | 120 | Calcium pantothenate | 2 |
| L-Valine | 150 | Pyridoxal . HCl | 1 |
| Carbon sources | | Thiamine . HCl | 1 |
| Glucose | 3000 | i-Inositol | 1 |
| Sodium pyruvate | 110 | Riboflavin | 0.1 |
| | | $B_{12}$ | 0.002 |

[1] Added aseptically as 5% solution.
[2] Added as a $\times$ 100 solution during medium preparation.

TABLE 2

Effect of Varying Cell Concentrations on Peak Infectivity and CF Titers of FMDV Type $C_3$ Resende

| Cell concentration (cells/ml) | MOI (PFU/cell) | Peak infectivity titers $\log_{10}$ PFU/ml | hr | Peak CF titers[a] ratio | hr |
|---|---|---|---|---|---|
| $1.7 + 10^6$ | $0.33 + 10^{-1}$ | 8.0 | 10 | 12 | 19 |
| $4.0 + 10^6$ | $0.25 + 10^{-1}$ | 8.9 | 12 | 48 | 12 |
| $8.7 + 10^6$ | $0.10 + 10^{-1}$ | 9.0 | 12 | 48 | 8 |

[a] CF: reciprocal of dilution showing a 50% complement-fixation antigen end-point.

TABLE 3

Growth of the Seven Types of FMDV at various Passage in BHK-S Cells[a]

| Virus | Passage history[b] | Plaque titer ($\log_{10}$ PFU/ml) | CF[c] |
|---|---|---|---|
| Asia | $BK_5$ | 8.0 | |
| SAT-1 | $BK_5$ | 8.1 | |
| SAT-2 | $BK_5$ | 7.4 | |
| SAT-3 | $LT_1,BK_2$ | 7.9 | |
| $A_{24}$ | bovine | 8.2 | 12 |
| $O_1$ | bovine | 7.5 | 24 |
| $C_3$ | bovine | 8.5 | 24 |

[a]BHK-S cells were used at $1.8 + 10^6$ cells/ml and infected at multiplicities of approximately $10^{-2}$ for all viruses. Virus was harvested when cultures were observed to have ≧70% CPE; i.e., from 20 to 23 hr PI.
[b]LT: lamb testes cell cultures, subscript indicates number of passages. Bovine: virus propagated only in bovine tongue epithelium was used as a virus source.
BK: bovine kidney cell cultures, subscript indicates number of passages.
[c]CF: reciprocal of dilution showing a 50% compliment-fixation antigen end-point.

TABLE 4

Comparison of Plaque and CF Titers of Foot-and-Mouth Disease Viruses Grown in BHK-S Cells[a]

| Virus[b] | Plaque titer ($\log_{10}$ PFU/ml) | Reciprocal CF titer[c] |
|---|---|---|
| $A_{24}$ Cruzeiro | 8.58 | 24 |
| $O_1$ Caseros | 8.50 | 32 |
| $C_3$ Resende | 8.89 | 40 |

[a]Inoculated with 0.1 PFU/cell at cell concentrations of $4.0 \times 10^6$/ml.
[b]All viruses were harvested 12 hr after inoculation of BHK-S cell viruses
[c]CF: reciprocal of dilution showing a 50% complement-fixation antigen end-point.

TABLE 5

Virus Neutralization Values of Sera Collected from Steers 55 Days After Administration of Trivalent FMD Vaccine

| Animal number | $A_{24}$ mouse[a] | $A_{24}$ PRNT[b] | $O_1$ mouse[a] | $O_1$ PRNT[b] | $C_3$ mouse[a] | $C_3$ PRNT[b] |
|---|---|---|---|---|---|---|
| 1 | 2.05 | 2.64 | 2.00 | 2.55 | 2.31 | 2.56 |
| 2 | 2.40 | 3.00 | 2.58 | 2.68 | 1.91 | 2.34 |
| 3 | 1.45 | 2.37 | 1.62 | 2.26 | 1.91 | 2.06 |
| 4 | 1.90 | 2.38 | 2.22 | 2.67 | 1.93 | 2.19 |
| 5 | 2.06 | 2.94 | 2.29 | 2.58 | 1.45 | 2.44 |
| 6 | 2.20 | 2.74 | 2.65 | 2.60 | 1.93 | 2.57 |

[a]Mouse neutralization test performed in suckling white mice. Sera were tested against 100 to 400 $MLD_{50}$ of $A_{24}$, $O_1$, and $C_3$ viruses. Titer reported is $\log_{10} PD_{50}$. (MLD = mouse lethal dose)
[b]Plaque reduction neutralization test. Titer reported is the $\log_{10}$ of the serum dilution calculated to neutralize 70% of the plaques.

TABLE 6

Virus Neutralization Values ($\log_{10}$ 50% Protective Dilution) of Sera Collected from Guinea Pigs 30 Days after Administration of Monovalent or Trivalent FMD Vaccine as Tested in Suckling White Mice[a]

| Virus | | Monovalent | Trivalent |
|---|---|---|---|
| $A_{24}$ | range | 3.19–4.24 | 2.22–3.80 |
| | mean | 3.64 | 2.96 |
| $O_1$ | range | 3.53–4.50 | 2.22–3.60 |
| | mean | 4.02 | 3.24 |
| $C_3$ | range | 3.23–4.16 | 2.23–3.80 |
| | mean | 3.84 | 2.91 |

[a]Sera were tested against 100 to 400 $MLD_{50}$ of $A_{24}$, $O_1$, and $C_3$ viruses. There were 12 guinea pigs in each monovalent vaccine group, and 13 in each trivalent group. (MLD = mouse lethal dose)

I claim:

1. A process for producing a vaccine comprising maintaining a viable culture of baby hamster kidney cells in a glutamine-free, serum-free, heat-stable medium formulated to meet the nutritional requirements of baby hamster kidney cells and containing only chemically definable ingredients, inoculating said culture with a foot-and-mouth disease virus, cultivating said virus in the cell culture, and recovering a harvest of virus therefrom.

2. A process for producing a veterinary vaccine comprising maintaining a viable culture of baby hamster kidney cells in a glutamine-free, serum-free, heat-stable medium, formulated to meet the nutritional requirements of baby hamster kidney cells and containing only chemically definable ingredients such as amino acids, salts, vitamins and carbon sources, inoculating said culture with a foot-and-mouth disease virus, cultivating said virus in the cell culture, and recovering a harvest of virus therefrom.

3. A process for producing a foot-and-mouth disease vaccine comprising maintaining a viable culture of baby hamster kidney cells in a glutamine-free, serum-free, heat-stable medium, inoculating said culture with a foot-and-mouth disease virus, cultivating said virus in the cell culture, and recovering the harvest of virus therefrom, the aforesaid heat-stable medium comprising the following components in substantially the amounts specified per liter of medium: 400 mg L-Alanine, 100 mg L-Arginine, HCl, 300 mg L-Asparagine, 75 mg L-Cysteine, HCl, 150 mg L-Glutamic Acid, 60 mg L-Histidine, HCl, 150 mg L-Isoleucine, 300 mg L-Leucine, 300 mg L-Lysine, 60 mg L-Methionine, 120 mg L-Phenylalanine, 300 mg L-Proline, 300 mg L-Serine, 135 mg L-Theronine, 60 mg L-Tryptophan, 120 mg L-Tyrosine, 150 mg L-Valine, 3000 mg Glucose, 110 mg Sodium pyruvate, 7400 mg NaCl, 400 mg KCl, 265 mg $CaCl_2\cdot 2H_2O$, 3 mg Ferric ammonium citrate, 275 mg $MgCl_2\cdot 6H_2O$, 300 mg $NaH_2PO_4\cdot H_2O$, 0.3 mg $ZnSO_4\cdot 7H_2O$, 10 mg Phenol red, 500 mg Methylcellulose, 15 cps, 1000 mg $NaHCO_3$, 1 mg D-Biotin, 50 mg Choline·Cl, 1 mg Folic acid, 1 mg Niacinamide, 2 mg Calcium pantothenate, 1 mg Pyridoxal·HCl, 1 mg Thiamine·HCl, 1 mg i-Inositol, 0.1 mg Riboflavin, 0.002 mg $B_{12}$.

4. The process of claim 3 in which the cell culture is inoculated with a foot-and-mouth disease virus type selected from the group consisting of $A_{24}$, $O_1$, $C_3$, SAT-1, SAT-2, SAT-3, and Asia.

* * * * *